United States Patent [19]

Duffett

[11] Patent Number: Plant 5,354

[45] Date of Patent: Nov. 20, 1984

[54] CHRYSANTHEMUM PLANT NAMED TABASCO

[75] Inventor: William E. Duffett, Salinas, Calif.

[73] Assignee: Yoder Brothers, Inc., Barberton, Ohio

[21] Appl. No.: 467,860

[22] Filed: Feb. 18, 1983

[51] Int. Cl.[3] ..... A01H 5/00

[52] U.S. Cl. ..... Plt./82

[58] Field of Search ..... Plt./82, 79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Tabasco having flat capitulum form; decorative capitulum type; orange red ray floret color; diameter across face of capitulum ranging from 100 to 120 mm. at maturity; uniform nine week photoperiodic flowering response to short days; tall plant height when grown as a pinched, disbud pot mum, and semi-spreading branching pattern.

3 Drawing Figures

The present invention comprises a new and distinct cultivar of *Chrysanthemum morifolium,* Ramat., named Tabasco.

Tabasco is a product of a planned breeding program which had the objective of creating new chrysanthemum cultivars for pinched disbud pot mum programs having decorative capitulum type, intense bronze floret color, nine week flowering response and the ability to produce commercially acceptable quality in year round programs. Such traits in combination were not present or required improvement in previously available commercial cultivars.

Tabasco was originated from a cross made in a controlled breeding program in Salinas, Calif. in 1977. The female parent was Mandarin (unpatented but commercially available), a bronze decorative mutation from Mandalay which was originated by the present inventor from a hybridization of Woking Scarlet and Pamplemousse. The male parent of Tabasco was Festival (unpatented but commercially available), a bronze decorative, with parents unknown.

Tabasco was discovered and selected as one flowering plant within the progeny of the stated cross by William E. Duffett on Nov. 17, 1978 in a controlled environment in Salinas, Calif.

The first act of asexual reproduction of Tabasco was accomplished when vegetative cuttings were taken from the initial selection in February 1979 in a controlled environment in Salinas, Calif. by a technician working under formulations established and supervised by William E. Duffett. Horticultural examination of selected units initiated June 1980 has demonstrated that the combination of characteristics as herein disclosed for Tabasco are firmly fixed and are retained through successive generations of asexual reproduction.

Tabasco has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Tabasco which in combination distinguish this chrysanthemum as a new and distinct cultivar:

(1) Flat capitulum form;

(2) Decorative capitulum type;

(3) Orange-red ray floret color;

(4) Diameter across face of capitulum ranging from 100 to 120 mm. at maturity;

(5) Uniform nine week photoperiodic flowering response to short days;

(6) Tall plant height, requiring 1-2 long day weeks prior to pinch and short days, and 2-3 applications of 2500 ppm B-9 after the beginning of short days to attain a flowered plant height of 30 to 40 cm., and (7) Semi-spreading branching pattern.

The accompanying photographic drawings depict typical foliage and inflorescence characteristics of Tabasco. Sheet 1 is a color photograph of a plant of Tabasco grown as a pinched disbud pot mum, with colors being as accurate as possible with renditions of this type. Sheet 2 is a black and white photograph of three views of the inflorescence of Tabasco. Sheet 3 shows the leaves of Tabasco in three stages of development (mature, intermediate, immature).

Of the many commercial cultivars known to the present inventor, the most similar in comparison to Tabasco is Mandarin. Reference is made to attached Chart A which compares certain characteristics of Tabasco to those same characteristics of Mandarin.

Tabasco displays a brighter ray floret color, a larger capitulum diameter, taller plant height, and a shorter flowering response period.

Mandarin exhibits a stronger, more spreading branching pattern, with similar capitulum form and type.

In the following description, color references are made to The Royal Horticultural Society Color Chart. The color values were determined between 10:00 A.M. and 10:30 A.M. on June 1, 1982 under 150 foot-candle light intensity at Salinas, Calif.

CLASSIFICATION:

Botanical: *Chrysanthemum morifolium,* Ramat., cv Tabasco.

Commercial: Disbud decorative pot mum.

INFLORESCENCE

Capitulum:

*Form.*—Flat.

*Type.*—Decorative.

*Diameter across face.*—100 To 120 mm.

Corolla of ray florets:

*Color (general tonality from a distance of three meters).*—Orange red.

*Color (abaxial).*—44A-43A-42A Oxidizing to 34A-B.

*Color (adaxial).*—164B Suffused with 167B.

*Shape.*—Oblong with rounded tip.

Corolla of disc florets:

*Color (mature).*—6A.

*Color (immature).*—154C.

Reproductive organs:

*Androecium.*—Present disc florets only; scant pollen.

*Gynoecium.*—Present both ray and disc florets.

PLANT

General appearance:

*Height.*—Tall; 30 to 40 cm. given 2 long day weeks before pinch and lights out, and 2-3 applications of 2500 ppm B-9 SP after lights out.

*Branching pattern.*—Prolific; semi-spreading.

Foliage:

*Color (abaxial).*—147A.

*Color (adaxial).*—147B.

*Shape.*—Moderately lobed; slightly serrate.

CHART A

COMPARISON OF TABASCO AND MANDARIN

| CULTIVAR | RAY FLORET COLOR | CAPITULUM FORM AND TYPE | BRANCHING PATTERN |
|---|---|---|---|
| TABASCO | ORANGE RED | FLAT DECORATIVE | SEMI-SPREADING |
| MANDARIN | BRONZE RED | FLAT DECORATIVE | SPREADING |

| CULTIVAR | DIAMETER ACROSS FACE OF CAPITULUM | PLANT HEIGHT | FLOWERING RESPONSE PERIOD |
|---|---|---|---|
| TABASCO | 100 to 120 mm. | TALL 30 to 40 cm. | 9 WEEKS |
| MANDARIN | 75 to 95 mm. | SHORT 20 to 30 cm. | 10 WEEKS |

COMPARISONS MADE OF PLANTS GROWN AS PINCHED DISBUD POT MUMS IN SALINAS, CALIFORNIA AND LEAMINGTON, CANADA

I claim:

1. A new and distinct cultivar of *Chrysanthemum morifolium,* Ramat., named Tabasco, as described and illustrated, and particularly characterized as to uniqueness by the combined characteristics of flat capitulum form; decorative capitulum type; orange red ray floret color; diameter across face of capitulum ranging fom 100 to 120 mm. at maturity; uniform nine week flowering response; tall plant height, and semi-spreading branching pattern.

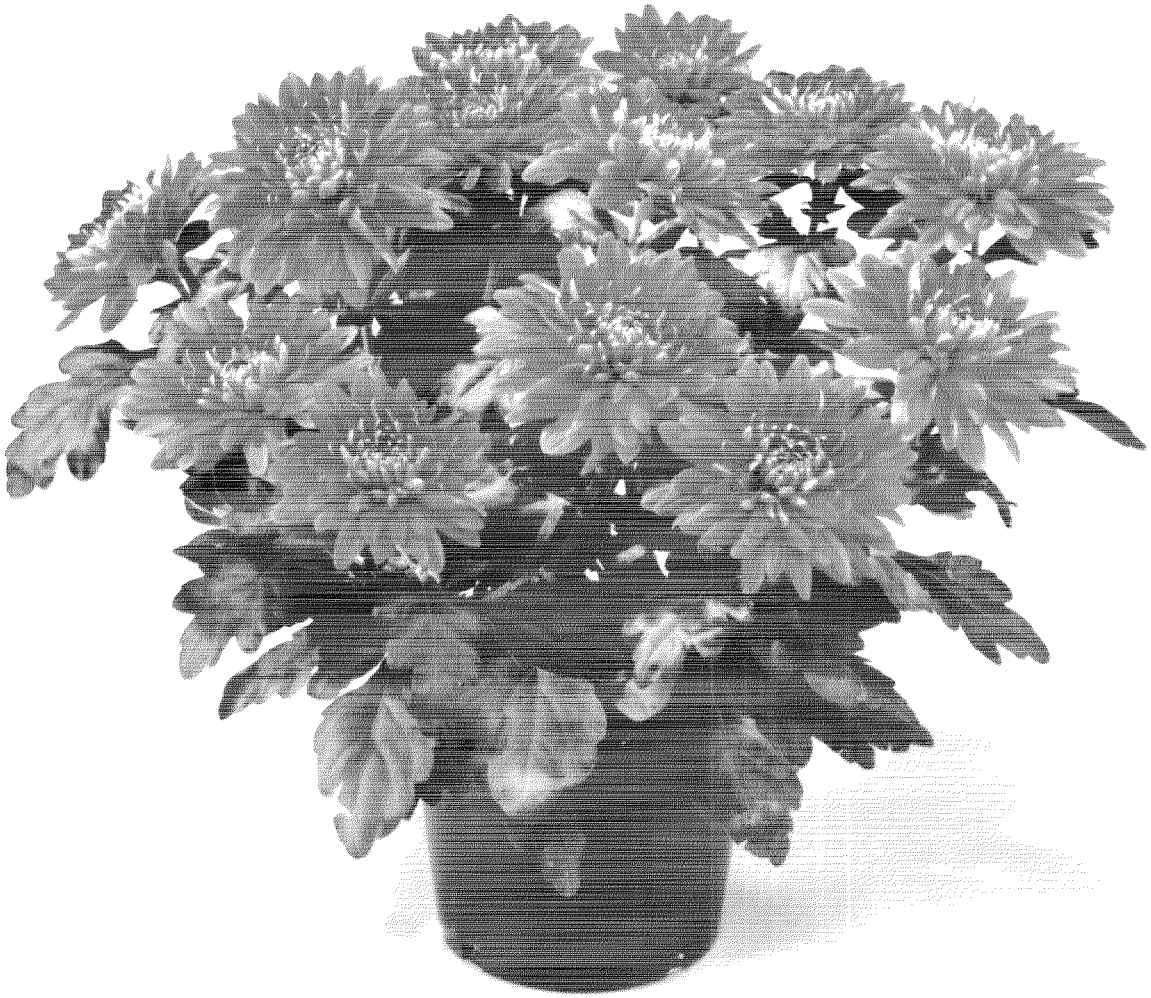

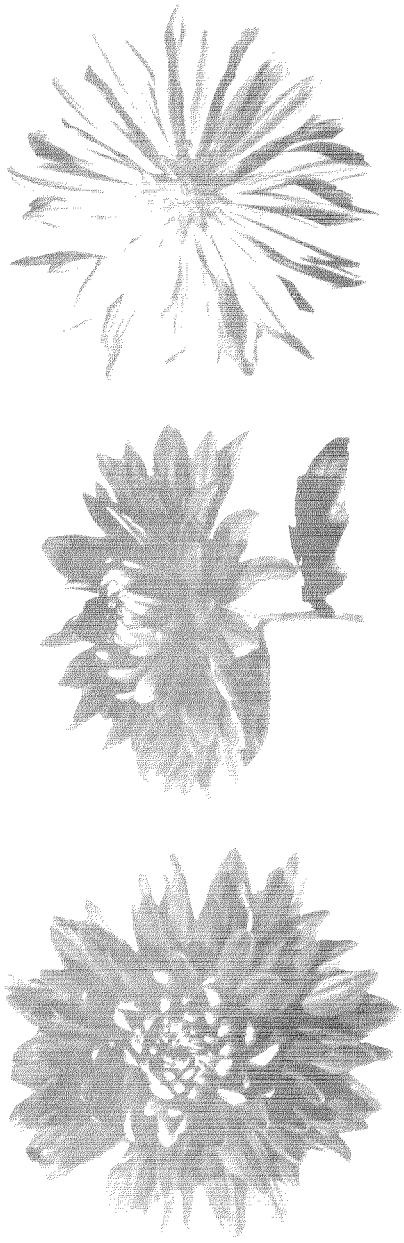

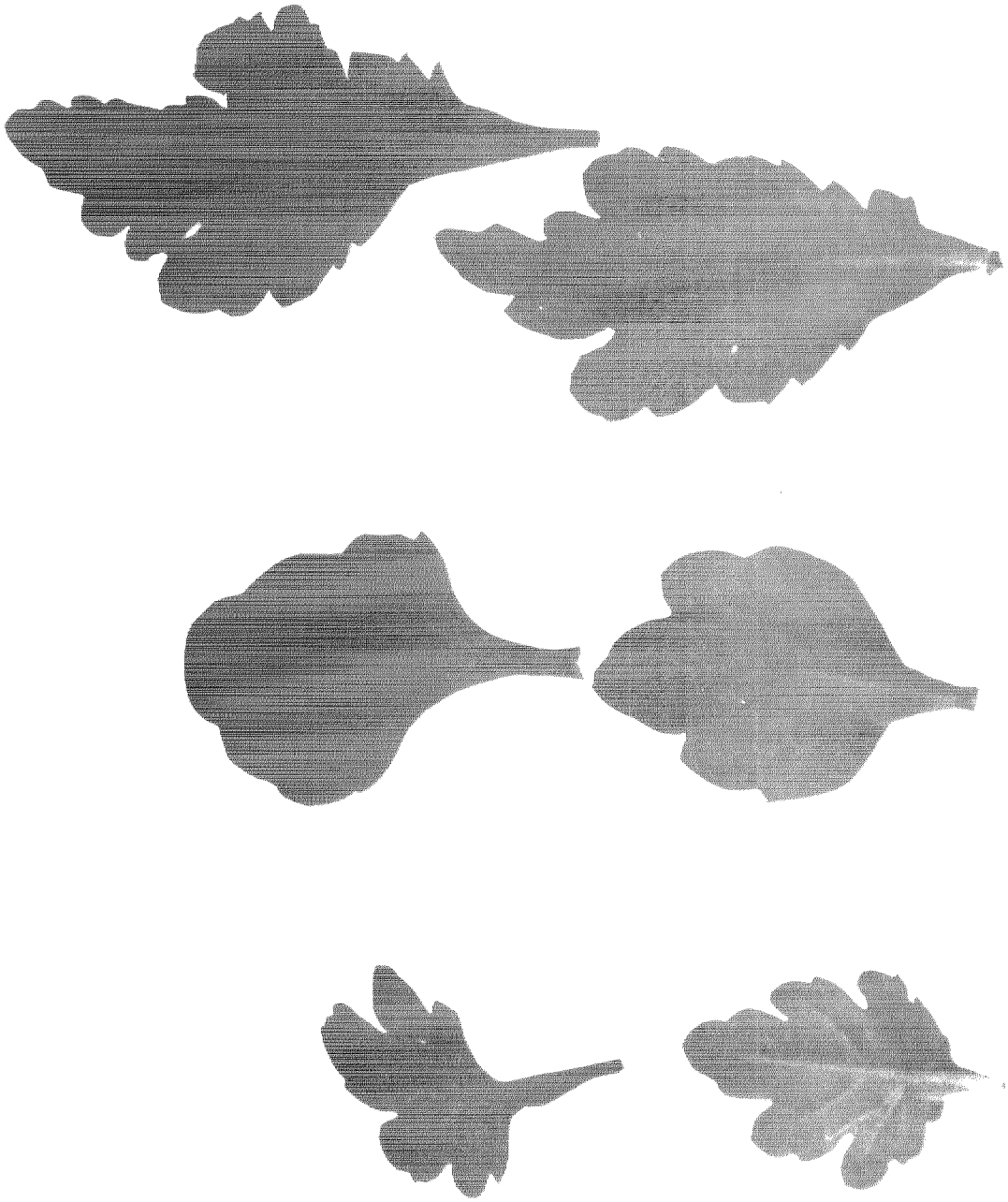

* * * * *